United States Patent [19]

Nashef et al.

[11] Patent Number: 4,786,287
[45] Date of Patent: Nov. 22, 1988

[54] PROCESS FOR DECREASING RESIDUAL ALDEHYDE LEVELS IN IMPLANTABLE BIOPROSTHETIC TISSUE

[75] Inventors: Aws S. Nashef, Costa Mesa; Ronald Dieck, Irvine, both of Calif.

[73] Assignee: Baxter Travenol Laboratories, Deerfield, Ill.

[21] Appl. No.: 917,503

[22] Filed: Oct. 10, 1986

[51] Int. Cl.$^4$ .................................................. C14C 3/32
[52] U.S. Cl. ...................................... 8/94.21; 8/94.2; 623/1; 623/2
[58] Field of Search ..................... 8/94.21, 94.17, 94.2, 8/94.19; 252/544; 623/1, 2, 3

[56] References Cited

U.S. PATENT DOCUMENTS

| | | | |
|---|---|---|---|
| 1,785,092 | 12/1930 | McLaughlin | 8/94.16 |
| 3,966,401 | 6/1976 | Hancock et al. | 8/94.11 |
| 3,988,782 | 11/1976 | Dardik et al. | 623/1 |
| 4,120,649 | 10/1978 | Schechter | 623/1 |
| 4,323,358 | 4/1982 | Lentz et al. | 8/94.11 |
| 4,402,697 | 9/1983 | Pollock et al. | 8/94.11 |
| 4,405,327 | 9/1983 | Pollock | 8/94.11 |
| 4,466,139 | 8/1984 | Ketharanathan | 623/1 |
| 4,481,009 | 11/1984 | Nashef | 8/94.11 |
| 4,553,974 | 11/1985 | Dewanjee | 623/1 |

OTHER PUBLICATIONS

Salgaller and Baipai, *Journal of Biomedical Materials Research*, vol. 19, 1–12 (1985).
Physical Biochemistry, 2nd Ed., D. Freifelder, W. H. Freeman and Co., San Francisco, 1982, pp. 257–260.
Wagner et al., *Biochem. Biophys. Res. Commun.*, 45, 184 (1971) Lindberg and Persson, *Eur. J. Biochem.* 31, 246 (1972).
Morrison and Boyd, *Organic Chemistry*, 3rd Ed., Allyn and Bacon, Inc., Boston, 1973, pp. 630–634.
Pharmacia P-L Biochemicals 1984 Product Reference Guide.
Bio-Rad Price List K, Jan. 1985.

*Primary Examiner*—Paul Lieberman
*Assistant Examiner*—John F. McNally
*Attorney, Agent, or Firm*—Bernard, Rothwell & Brown

[57] ABSTRACT

Residual aldehyde levels in bioprosthetic tissue are reduced by contacting the tissue with a rinsing solution such that aldehyde which has diffused out of the tissue into the rinsing solution comes into contact with, and reacts with, an amine, thus causing further diffusion of aldehyde out of said tissue. The amine may be dissolved in said rinsing solution or may be immobilized on a solid support to which the rinsing solution is periodically or continuously exposed.

32 Claims, No Drawings

PROCESS FOR DECREASING RESIDUAL ALDEHYDE LEVELS IN IMPLANTABLE BIOPROSTHETIC TISSUE

TECHNICAL FIELD

The present invention relates to a method for preparing biological tissue for surgical implantation in bioprosthetic applications. More specifically, the present invention provides a method for reducing residual aldehyde levels in bioprosthetic tissue which has been contacted with an aldehyde during pre-implantation processing.

BACKGROUND OF THE INVENTION

Surgical implantation of biological tissue is well known, and has many clinical applications. The source of the tissue may be the patient himself (autologous tissue), a member of the same species as the patient (homologous tissue), or a member of a different species (heterologous tissue). Examples of tissues which have been implanted as bioprosthetic materials are tendons, ligaments, heart valves, bone, skin patches, collagen, pericardial tissue patches, arteries, and many others. The introduction of methods for rendering tissues non-antigenic has made it possible to transplant tissue derived from various animal species into humans to repair or replace defective body parts.

The preparation of biological tissue for implantation frequently includes treatment with a chemical agent that "fixes" (i.e., "tans") the tissue. Various aldehydes have been used for this purpose, including glyoxal, formaldehyde, dialdehyde starch, and glutaraldehyde. Glutaraldehyde is considered by many to be the preferred tanning agent, and is also used as a tissue sterilant, having proven to be a good barrier against microbial contamination. Glutaraldehyde treatment is also known to render tissue substantially non-antigenic so that transplanted heterologous tissue does not elicit an adverse immune response in the recipient. Aldehyde-treated tissue is commonly rinsed with sterile distilled water or a solution such as saline prior to surgical implantation, in an attempt to remove residual aldehyde compounds from the tissue. Certain post-implantation problems, such as inflammation and other adverse reactions in some patients, are believed in some cases to be caused by residual aldehyde in implanted bioprosthetic tissue.

SUMMARY OF THE INVENTION

The present invention provides an improved method for reducing residual aldehyde levels in implantable biological tissues which have been treated with aldehydes during pre-implantation chemical processing procedures. The method comprises contacting the tissue with an amine-containing solution such that the amine compound reacts with the aldehyde compound which has leached out of the tissue, thus promoting further diffusion of unbound residual aldehyde out of the tissue. Binding of the aldehyde by the amine in the rinsing solution maintains an equilibrium favoring diffusion of additional unbound aldehyde out of the tissue. The amine compound may be dissolved or dispersed in the rinsing solution, or may be coupled to a solid support to which the rinsing solution is periodically or continuously exposed.

DETAILED DESCRIPTION OF THE INVENTION

The present invention relates to a process for decreasing residual aldehyde levels in bioprosthetic tissue prior to surgical implantation of the tissue. The process comprises contacting the tissue (which previously has been treated with an aldehyde) with a solution comprising a compound which will react with the aldehyde compound without harming the biological tissue. Many types of compounds which are reactive with aldehydes are known to one skilled in the art (see, for example, Morrison and Boyd, *Organic Chemistry*, 3rd Ed., Allyn and Bacon, Inc., Boston, 1973, pp. 630–634, herein incorporated by reference). Preferably, the tissue is contacted with a solution comprising an amine such that the unbound aldehyde which diffuses out of the tissue reacts with the amine. Binding of the aldehyde in the rinsing solution by the amine (through chemical reaction) is thought to create a concentration gradient which promotes further diffusion of aldehyde out of the tissue. The amount of residual unbound aldehyde which diffuses out of the tissue is thus greater than the amount that would diffuse out of the tissue if the rinse solution lacked a compound which reacts with the aldehyde. Using the method of the present invention, the residual glutaraldehyde levels and cytotoxicity of glutaraldehyde-treated tissues have been greatly diminished when compared to glutaraldehyde-treated tissues rinsed conventionally in saline for similar periods of time.

The biological tissue which is to be implanted may be derived from many different animal species. Suitable sources include, but are not limited to, bovine, porcine, equine, ovine, kangaroo, rabbit, or human tissues. The tissue may be epithelial or fibrous connective tissue, such as pericardial tissue, dura mater, fascia lata, amnion, tendon, ligament, cartilage, and the like. Alternatively, collagen (including reconstituted collagen and collagen when backed by synthetic fabric), may be used. Many other tissue types, including arteries, veins, skin patches, and bone, are also known to have bioprosthetic uses.

The tissue is extracted from its source and processed by one of many known procedures used to prepare biological tissue for implantation as bioprosthetic material. These tissue handling conditions are conventional, and are not considered to be part of the present invention. In general, the tissue is extracted from the animal source, and extraneous material (e.g., fat) is removed. The tissue is then transported, stored, and processed under physiologically acceptable conditions of temperature and pH, i.e., conditions that are not deleterious to the tissue components. A preferred pH range is from about 7.0 to about 7.6, with a pH of 7.1 to 7.4 being most preferred.

Buffers which contact the tissue should not interfere with any of the processing steps. Such buffers have a buffering capacity sufficient to maintain a physiologically acceptable pH, particularly during the fixation of the tissue. The choice of the appropriate buffer and its concentration will depend upon specific tissue preparation conditions, and variations of these buffers have been introduced by several manufacturers. The buffer can be either conventional 0.01–0.02M phosphate-buffered saline (PBS) or phosphate-deficient solutions such as those containing less phosphate than these 0.01 to 0.02M PBS solutions, and preferably less than about 0.001 to about 0.002M phosphate. Preferred buffers in accordance with the present invention include borate, carbonate, bicarbonate, cacodylate (found to be non-toxic in animals), and other synthetic, artificial, or organic buffers such as N-2-hydroxyethylpiperazine-N'-2-ethanesulphonic acid (HEPES); morpholine propanesulphonic acid (MOPS); and 1,4- piperazinediethanesulphonic acid (PIPES). Preferably, the buffered or unbuffered solutions used in accordance with the present invention should not interfere with the tissue-stabilizing process afforded by the fixing agents such as glutaraldehyde. That is, they should not react with the fixing agent or prevent the fixing agent from achieving proper fixation of the tissue. Illustrative of these unsuitable buffers are those containing primary and secondary amines such as tris(hydroxymethyl)aminomethane (tris), which react with the aldehyde groups of glutaraldehyde and thus interfere with the normal tissue stabilization process.

Treatment of extracted biological tissue with aldehyde compounds (e.g., to fix and/or sterilize the tissue) is well-known in the art, and forms no part of the present invention. Procedures for such treatment are given, for example, in U.S. Pat. Nos. 4,120,649; 3,988,782; and 4,553,974, each of which is incorporated herein by reference. Glutaraldehyde is the preferred fixing agent and the tissue advantageously is contacted with a buffered solution containing from about 0.2 to about 0.8 percent (w/v), preferably about 0.6 percent (w/v) glutaraldehyde. The tissue advantageously is contacted with the glutaraldehyde for at least a time sufficient to cross-link proteins in the tissue to a degree sufficient to stabilize the tissue and to render it substantially non-antigenic.

The processing procedures may vary according to the type of tissue being processed and its intended application. For example, soft biological tissues may be chemically treated according to any of several known procedures to mitigate post-implantation calcification of the bioprosthetic tissue. Such calcification mitigation treatments are described in, for example, U.S. Pat. Nos. 4,323,358 and 4,481,009.

The tissue can be sterilized by any conventional means, including exposure to ethylene oxide or immersion in a solution containing glutaraldehyde or formaldehyde. A sterilizing solution containing from about 0.2 to about 1% glutaraldehyde or about 4-5% formaldehyde may contain additional substances such as ethanol, surfactants, and buffering compounds. Alternatively, tissue can be sterilized by exposure of frozen or freeze-dried tissue samples to gamma-irradiation.

The order of the processing steps may vary. Once the sterilization step has been performed, the tissue must, of course, be maintained under sterile conditions and contacted only with sterile solutions and reagents. After the tissue has been treated according to the method of the invention to reduce residual aldehyde levels, the tissue should not, of course, be contacted with any aldehyde compound in a subsequent step. For example, the tissue should not be treated with a sterilizing solution containing glutaraldehyde or formaldehyde after the treatment to reduce residual aldehyde levels has been completed.

Tissue which has been contacted with an aldehyde during pre-implantation processing is then treated by the method of the present invention to reduce residual aldehyde levels in the tissue prior to surgical implantation. A high residual level of glutaraldehyde in bioprosthetic tissue is thought to be a cause of certain adverse host reactions, such as inflammation in surrounding host tissues, after implantation of bioprostheses. Indeed, glutaraldehyde-tanned bioprosthetic tissues have shown high cytotoxicity (as measured by in vitro assays) when post-tanning rinses were conventional rinses in saline solution, as often practiced in the art. Removal of residual glutaraldehyde is particularly difficult for thick and/or dense biological tissues, such as ligaments. Using the method of the present invention, residual glutaraldehyde levels have been substantially reduced in bioprosthetic tissues, including ligaments, as described in the "Examples" below. Reduction of residual aldehyde to acceptable levels is accomplished in a relatively short time.

In accordance with the method of the present invention, aldehyde-treated biological tissue is contacted with a rinsing solution containing an amine compound. Such amine compounds include compounds which contain one or more aldehyde-reactive amino groups. The amine compound may be a primary or secondary amine. Advantageously, amines which react efficiently with aldehyde compounds are used in the method of the invention. Primary amines are generally more reactive with aldehydes than are secondary amines, and primary amines therefore are preferred. Primary amines have the general formula R—NH$_2$, where R can be an aliphatic (straight-chain or branched) or aromatic group, or a combination thereof. Examples of aliphatic primary amines are methylamine, ethylenediamine, tert-butylamine, ethanolamine, hydroxylamine, and many others known to those skilled in the art. Examples of aromatic primary amines are phenylhydrazine, aniline, toluidine, anisidine, and many others. The rate of reaction of the amine with the aldehyde groups is influenced by the bulk of the R group and by the solubility of the amine compound. In general, the more soluble the amine, and the smaller the R group, the more reactive the compound is, and, therefore, the more preferable the amine compound is for use in the invention. Amines having R groups which are electron-donating, as opposed to electron-withdrawing, are also preferred, because they are more basic, and therefore more reactive in nucleophilic additions to a carbonyl group of an aldehyde.

Since many amines are known to be toxic, the toxicity of a particular amine, and of the product of its reaction with an aldehyde, should be considered. When the amine compound is free in the rinsing solution, a non-toxic amine should be chosen for use, since the amine will be in contact with biological tissue which is to be implanted in a living host, and residues of the amine may remain in the implantable tissue. If the amine is bound to a solid support, in accordance with an alternative embodiment of the invention, relatively toxic amines could be used as long as the bond to the solid support is stable and non-reversible so that the amine compounds could not become free in the solution. Primary amines which are non-toxic and therefore preferred for use in the method of the invention include the amino acids, many of which are commercially available. The most preferred primary amine compound is tris(hydroxymethyl)aminomethane ("tris"), which is a commercially available buffering compound, and is particularly preferred because of its reactivity and its non-toxicity. This compound is sold under the trademark Trizma ® by Sigma Chemical Company of St. Louis, Mo., for example.

As discussed in more detail below, the volume of rinsing solution, the concentration of amine, and the number and duration of rinses used in the method of the present invention are interrelated, in that one advantageously should consider the other parameters in this group when selecting any one parameter in the group. For example, a decrease in any one (i.e., in the volume, the amine concentration, or the number or duration of the rinses) would generally reduce the efficiency of residual aldehyde removal from the tissue, but such a decrease may be offset by an increase in one or more of the other parameters.

The amine compound may be dissolved in the rinsing solution or may be attached to a solid support. The amine should be present in the rinsing solution or on the support in a concentration sufficient to react with substantially all of the residual free aldehyde groups in the tissue. Preferably, the concentration of the amine compound is such that there is a stoichiometric excess of the amino groups over the residual free aldehyde groups. Good results have been achieved using a rinsing solution containing more than a 100-fold excess of amino groups over the residual aldehyde groups. Preferably, the amine groups are present in at least a 5-fold excess over the residual free aldehyde groups. Residual aldehyde in aldehyde-treated bioprosthetic tissue may be measured by immersing a piece of the bioprosthetic tissue in a liquid such as saline for approximately 24 hours, then determining the amount of aldehyde in the solution by standard gas chromatography techniques. The amine concentration in the rinsing solution may vary considerably and still be effective in binding aldehydes leaching from biological tissue and promoting further diffusion of aldehydes out of the tissue according to the method of the invention. Advantageously, however, the amine concentration is high enough to promote removal of residual aldehyde from the tissue within a relatively short time. In general, the lower the concentration of a particular amine, the longer the total rinsing time will be. The amine concentration may also vary according to the ratio of tissue weight and surface area to solution volume. As the solution volume for rinsing a particular piece of tissue decreases, the amine concentration in the solution would have to increase to keep the total rinsing time the same. In addition, the amine concentration may vary according to the number of rinses (i.e., the number of fresh changes of amine solution in which the tissue is immersed), with the number of rinses required decreasing as the amine concentration increases. Likewise, if the rinsing solution is constantly replenished, a lower amine concentration may be used. As discussed above, the reactivity of the various amine compounds toward aldehydes varies. Therefore, higher concentrations of the less reactive amines would be used to reduce aldehyde levels to an acceptable level in a desirably short period of time.

Effective amine concentrations typically range from about 0.001M to about 1M, preferably about 0.1M. Most preferably, the rinsing solution comprises 0.1M tris buffer, pH 7.4. The rinsing solution should be buffered and the pH of the solution should be maintained within a physiologically acceptable range, as described above. When tris is used as the amine, it also serves as a buffer.

In accordance with the present invention, the biological tissue is immersed in a volume of rinsing solution, which, together with the amine concentration and number of rinses (as explained above), is sufficient to promote efficient diffusion of residual aldehyde out of the tissue. Thus, the volume of rinsing solution may vary.

A lower aliphatic alcohol, such as ethanol, optionally may be added to the rinsing solution, as shown in Example I below. However, residual alcohol in the tissue may cause cytotoxicity if it is not sufficiently removed from the tissue prior to use, so the rinsing solution preferably is alcohol-free.

In one embodiment of the invention, biological tissue which has been subjected to processing which includes tanning (with an aldehyde) and sterilizing steps is rinsed in 100 mls. of a sterile 0.1M tris solution per 10 grams (wet weight) of the tissue, under aseptic conditions, with several changes of the rinsing solution (e.g., from three to five rinses for from about 10 minutes to about 1 hour each, followed by one rinse for about 16 hours or more). Good results have been achieved using 10-minute rinses. Shorter rinses are advantageous in that the bioprosthetic tissue is ready for implantation in a shorter amount of time. Shorter rinsing procedures are especially beneficial to commercial enterprises engaged in the large-scale preparation of bioprosthetic tissue. Also, when the tissue is rinsed under aseptic conditions, shorter rinsing times are advantageous. If the tissue (which now has reduced residual aldehyde levels) is not to be implanted immediately, it may be packaged (stored) in any suitable aldehyde-free sterile solution. Suitable solutions include those containing tris and ethanol (e.g., 0.1M tris/50% ethanol or 0.1M tris/70% ethanol), or preferably, tris alone (e.g., 0.1M tris). The advantages of packaging the tissue in tris alone are discussed in the examples below. Tissue stored in tris can be implanted directly from the storage solution, or may be rinsed briefly in normal saline (e.g., 3 rinses for 5 minutes each, or immersed in one saline rinse for 5 to 10 seconds). If the storage solution contains alcohol, then the tissue should be rinsed (e.g., a minimum of 3 rinses for 5 minutes each in normal saline) to remove residual alcohol before implantation. Alternatively, the tissue could be rinsed in a sterile tris solution, rather than saline, immediately prior to implantation. In accordance with one embodiment of the invention, good results have been achieved by rinsing tanned and sterilized tissue 5 times, for one hour per rinse, followed by one 16-hour rinse, in 0.1M tris, then storing the tissue in 0.1M tris, followed by either no rinsing or one 5-10 second immersion in normal saline. The thus-treated tissue demonstrates low cytotoxicity, as explained in more detail in the examples section below.

The rinsing solution may be reused so long as reactive amino groups are present. A standard ninhydrin assay may be used to determine whether free amine has been depleted. Preferably, a large excess (e.g., 100-fold) of amine over aldehyde is used, so that the amine will not be depleted, and testing will not be necessary. The more often the solution is changed, and/or the larger the volume of solution contacting the tissue, the shorter the total rinsing time will be. Alternatively, the tissue may be immersed in a rinse solution which is constantly replenished, e.g., in a tank into which fresh solution is constantly added at the same rate at which solution is draining from the tank through an outlet. Rinsing continues until residual aldehyde levels have been decreased to a level at which the bioprosthetic tissue is substantially non-cytotoxic, as explained below. Preferably, residual aldehyde levels are decreased to about 1 part per million (ppm) or less. Residual aldehyde levels can be measured by any known means, including gas chromatography. For example, a sample of tissue rinsed in tris according to the method of the present invention may be transferred to saline solution for 24 hours, and the level of aldehyde which has leached into the solution is then measured by gas chromatography.

In an alternative embodiment of the invention, the amine compound is immobilized, e.g., by attachment to a solid particulate support. The resulting solid material may be packed into a column or bed through which a tissue rinsing solution is percolated. Preferably, a slurry of the solid immobilized amine material in a buffered solution is prepared, and the tissue is immersed in the slurry. The slurry then is circulated around the tissue by any suitable means, e.g., by automatic stirring devices.

Several solid support materials having free amino-group-containing ligands bound thereto are available commercially. Examples of these materials are agarose-butylamine (e.g., AGBUTYLAMINE ™), agarose-decylamine (e.g., AGDECYLAMINE ™), agarose-ethylamine (e.g., AGETHYLAMINE ™), agarose-adipic acid hydrazide, agarose to which 1,6-diaminohexane is coupled ([Sepharose 4B]—NH—$(CH_2)_6$—$NH_2$, sold as AH-Sepharose 4B), Arginine-Sepharose 4B (agarose having the amino acid arginine bound thereto), and Lysine-Sepharose 4B (lysine bound to agarose), all available from Pharmacia P-L Biochemicals in Piscataway, N.J. Sepharose 4B designates a highly porous beaded agarose, at a concentration of 4% in the commercial preparation. Other such materials include amino terminal agarose (e.g., Affi-Gel 102, an amino terminal agarose gel with a hydrophilic spacer arm, having the formula: [agarose]—$OCH_2CONH(CH_2)_2NH_2$) or aminoethyl polyacrylamide gels (e.g., aminoethyl Bio-Gel P-2 or P-150, which have the formula: [polyacrylamide]—$CONHCH_2CH_2NH_2$, where the polyacrylamide is Bio-Gel P-2, 200–400 mesh, or Bio-Gel P-150, 100–200 mesh.) These materials are available from Bio-Rad Laboratories, Richmond, Calif.

Alternatively, the solid support material and an amine compound may be obtained separately, and the amine may be bound to the support by a variety of known techniques, depending on the particular amine and support chosen. The preparation of solid supports having desired compounds ("ligands") bound thereto is well known for use in affinity chromatography procedures. See, for example, *Physical Biochemistry*, 2nd Ed., D. Freifelder, W. H. Freeman and Co., San Francisco, 1982, pp. 257–260. Many solid support materials having an amine compound attached thereto may be prepared for use in the method of the invention. The amine compound is bound to the support material, either directly or through a "spacer" compound, such that free amine groups remain after binding to the support is completed. The bond advantageously is non-reversible.

The solid support material may be any suitable material which would not release toxic substances into the rinse solution. Such suitable materials include polyacrylamide and agarose, many types of which are commercially available from, for example, Pharmacia P-L Biochemicals, Piscataway, N.J., and BioRad Laboratories, Richmond, Calif. The linkage between the amine compound and the support may be accomplished by a variety of chemical reactions. One such known chemical reaction is cyanogen bromide activation of agarose, followed by reaction of the cyanogen bromide with amino groups on a ligand to bind the ligand to the solid support. Cyanogen bromide-activated agarose is commercially available (e.g., from Pharmacia P-L Biochemicals, Inc., Piscataway, N.J., U.S.A.) and readily couples primary amino groups. Therefore, diamine compounds (e.g., ethylenediamine, amino acids such as lysine or hydroxylysine, and many other compounds) can react with the activated agarose, and be bound thereto, and still have a free amino group. A polypeptide such as polylysine also may be coupled to the support, to provide a large number of free amine groups. The linkage of ligands to cyanogen bromide activated material is described in Wagner et al. (*Biochem. Biophys. Res. Commun.*, 45, 184 [1971]), and Lindberg and Persson (Eur. J. Biochem., 31, 246 [1972]). Alternatively, a diamine compound may be attached to a solid support material having free carboxyl groups, through a carbodiimide reaction. Such solid supports include, among others, agarose having 6-amino-hexanoic acid coupled thereto ([Sepharose 4B]—NH—$(CH_2)_5$—COOH, solid as CH-Sepharose-4B by Pharmacia P-L Biochemicals) and carboxymethyl agarose ([agarose]—$OCH_2COOH$) or carboxyl terminal agarose ([agarose]—$OCH_2CONH(CH_2)_2NHCO(CH_2)_2COOH$), both available from Bio-Rad Laboratories. The use of a carbodiimide coupling reagent (e.g., 1-ethyl-3(3-dimethylaminopropyl) carbodiimide hydrochloride) to link ligands to such supports is well known.

To minimize possible steric hindrance of the reaction between the amino groups and the aldehyde compounds, the free amino groups attached to the solid support should not be too near the solid-matrix surface. Thus, solid materials such as agarose-decylamine or AH-Sepharose 4B (described above), which have "spacers", comprising a carbon chain of ten and six carbon atoms, respectively, between the agarose surface and the free amino group, are generally preferred over such materials as agarose-ethylamine, which has only a 2-carbon spacer.

One skilled in the art will recognize the wide variety of solid supports having ligands attached thereto which have free amino groups, which can be used in the method of the invention. According to this embodiment of the invention, the tissue is immersed in a rinsing solution which may be any suitable physiologically-compatible solution, such as distilled water, saline, phosphate-buffered saline, HEPES-buffered solution, or other buffered solution. To achieve the advantages of the immobilized amine embodiment (discussed below), the rinsing solution should be amine-free. The rinsing solution flows over both the tissue and the immobilized amine (the amine attached to the solid support). The aldehyde which has diffused out of the tissue into the rinsing solution therefore comes into contact with the immobilized amine, and is bound by the amine. The immobilized amine therefore removes free aldehyde from the solution, thereby promoting diffusion of additional aldehyde out of the tissue. The immobilized amine advantageously is in the same container as the tissue, with the immobilized amine material added to the rinsing solution to form a slurry. Alternatively, the immobilized amine, which may be packed into a column or bed, may be in a separate container connected, e.g., by tubing, to the container into which the tissue is placed, and the rinsing solution is cycled through both containers. If the tissue is sterilized prior to the rinsing procedure, the tissue, immobilized amine, and sterile rinsing solution all may be contained in a closed system, so that aseptic conditions can be maintained.

The interrelationship of the volume of rinsing solution, the amine concentration, and number and duration of the rinses, is generally as described above (in the description of the free-amine-containing rinsing solution embodiment). Of course, if the available free amino groups are depleted through reaction with aldehydes, the amine compound is replenished by replacing the solid (immobilized amine) material, rather than changing the rinsing solution as before. Preferably, the amount of free amino groups bound to the solid support is such that there is a large excess (e.g., 100-fold) of amino groups over residual aldehyde groups.

Whether the amine is bound or free in solution, the principle of the invention is the same. When unbound aldehyde which has diffused out of the biological tissue is bound by the amine, the diffusion equilibrium promotes the diffusion of additional aldehyde out of the tissue. The immobilized amine embodiment has the advantage that neither the amine nor the amine-aldehyde complex actually comes into contact with the biological tissue, and therefore will not become entrapped within the tissue. Also, the amine will not bind to the tissue by reaction with reactive groups on the tissue.

When aldehyde-treated tissue is treated according to the method of the present invention, residual aldehyde is decreased to levels significantly below the residual aldehyde levels in tissue rinsed with amine-free solutions, as demonstrated in the "Examples" below. The amount of rinsing time required to reduce residual aldehyde to an acceptable level is relatively short when the herein-disclosed method is employed, which is particularly beneficial to commercial enterprises in which bioprosthetic tissue is prepared on a large scale.

The temperature of the rinsing solution may vary considerably. Slightly elevated temperatures may be employed advantageously, and may reduce the total rinsing time required, provided that the temperature is not so high as to cause deleterious effects on the tissue. In general, the temperature is maintained from about 4° C. to about 45° C. Preferably, the temperature is about 35±2° C.

The rinsing solution is preferably sterilized (by standard methods such as autoclaving) prior to contacting the tissue, and all rinsing steps are carried out under aseptic conditions. The bioprosthesis is then ready for implantation. Alternatively, the rinsed tissue may be stored until needed, preferably in 0.1M tris, pH 7.4, as described above.

The following Examples are provided to illustrate specific embodiments of the method of the present invention, and are not to be construed as limiting the scope of the invention. One skilled in the art will readily appreciate variations in the procedures described below which would fall within the scope of the invention described and claimed herein.

EXAMPLE I

Extracted bovine ligament tissue was purchased from Xenomedica, Lucerne, Switzerland. The tissue had been tanned in approximately 0.2% (w/v) glutaraldehyde for one year or more. The ligaments were sterilized by immersion in a sterilant solution comorising about 1% glutaraldehyde and 22.5% isopropanol for approximately 48 hours at 37° C. Twenty-four samples of the ligaments then were rinsed according to the method of the present invention to reduce residual glutaraldehyde levels. The parameters of the rinsing procedure varied for each sample, as shown under "production rinses" in Tables I and II. The number of rinses varied, and the rinsing solution comprised either 0.1M tris, pH 7.4/50% ethanol, 0.1M tris, pH 7.4/70% ethanol, or 0.1M tris, pH 7.4. Samples were rinsed with 100 mls. (per rinse) of rinsing solution per 10 grams (wet weight) of tissue.

The ligaments then were packaged in one of the three solutions listed above, and stored at room temperature for 15 days. The samples then were removed from the storage solutions for cytotoxicity evaluation. Eighteen samples were rinsed conventionally in 300 mls/sample of saline (either 3 rinses of 5 minutes each or a single rinse of 5 to 10 seconds (a "quick dip"). These two types of "clinical rinses" simulate rinsing procedures commonly practiced by surgeons in the operating room for rinsing prostheses just prior to implantation. The remaining six samples were not rinsed after removal from storage solution.

The samples then were analyzed for cytotoxicity using an "agar overlay" method designed for cytotoxicity scoring of diffusible components in solid samples. The general procedure for the agar overlay test is described by Guess et al. ("Agar Diffusion Method for Toxicity Screening of Plastics on Cultured Cell Monolayers", *J. Pharm. Sci.*, 54:1545 [1965]). Two 1-centimeter pieces were cut from each ligament following the clinical saline rinses (or immediately after removal from the packaging solution for the six samples not clinically rinsed in saline) and were gently placed on an agar plate. Each agar plate had been previously prepared by cultivating mammalian cells thereon to form a cell monolayer on the agar surface, then staining the cells with a dye. After the ligament samples were placed on the agar plates, the plates were incubated at 37±1° C. in a humidified atmosphere containing 4–6% $CO_2$ for 24±1 hours. The plates then are examined microscopically at 100X for the percent of cells lysed in the vicinity of each ligament sample. Empty areas between cells are indicative of cell lysis.

In addition to cytotoxicity evaluation, the ligaments were analyzed for residual glutaraldehyde, ethanol (for those samples contacted with ethanol during processing) and isopropanol (which contacted the samples during the sterilizing step). Pieces were cut from each ligament and immersed in saline solution (in separate containers). After 24 hours at room temperature, the saline solution was analyzed for glutaraldehyde, isopropanol, and ethanol content using known gas chromotography procedures. Each of the 24 samples were found to have less than 1 part per million (ppm) residual glutaraldehyde. All but five of the samples had less than 1 ppm residual isopropanol, with the five samples having from 1.5 to 7.6 ppm isopropanol. Residual ethanol levels were found to be highest in samples contacted with ethanol during both production rinse procedures (i.e., the rinsing procedures according to the invention to remove residual aldehyde) and packaging, especially when rinsed by a "quick dip" in saline (as opposed to 3×5 minute rinses in saline) after removal from the package.

The results of the analysis for residual ethanol are presented in Tables I and II, along with the cytotoxicity results. The best results (i.e., 0% cytotoxicity) all were achieved when ligaments were packaged in 0.1M tris, pH 7.4 (Table II), rather than in 0.1M tris/ethanol solutions (Table I). When ligaments were packaged in tris alone (i.e., without ethanol), rinsing with saline did not, generally, improve cytotoxicity results (compared to ligaments not rinsed in saline), and saline rinses therefore were found to be unnecessary in these cases.

When tissues were packaged in tris/ethanol solutions, then rinsed by a "quick dip" (i.e. 5-10 seconds) in saline, the samples generally demonstrated moderate to severe cytotoxicity (Table I). This cytotoxicity apparently resulted from relatively high residual ethanol levels (as shown in Table I) due to the insufficiency of the quick rinse for removing residual ethanol. Similarly treated tissue rinsed three times in saline for 5 minutes per rinse generally showed lower residual ethanol levels than those rinsed by a quick dip, and showed mild toxicity.

EXAMPLE II

Extracted bovine tendons were rinsed and shipped in normal saline. The ligaments were then fixed by immersion in 0.625 weight percent glutaraldehyde in an isotonic solution containing 5.39 grams/liter of the sodium salt of HEPES, 0.440 weight percent sodium chloride, and 2.6 grams/liter of $MgCl_2.6H_2O$ at room temperature.

The tanned ligaments were divided into four groups. Three groups were rinsed under sterile conditions in 0.1M tris buffer, pH 7.4, at 37° C., as follows:

Group #1: rinsed each ligament separately, four times for 10 minutes per rinse, in 100 mls rinse solution Group #2: rinsed each ligament for 16 hours in 100 mls rinse solution Group #3: rinsed each ligament for 24 hours in 100 mls rinse solution The ligaments in groups 1 through 3 were then subjected to standard clinical rinses (three rinses for 10 minutes each in sterile saline).

The fourth group was rinsed three times, for 10 minutes per rinse, in sterile saline. This group was rinsed only in an amine-free solution commonly used for such purposes, to compare residual glutaraldehyde levels with ligaments in groups 1 through 3 which were rinsed according to the method of the present invention.

Bioprosthetic ligaments from all four groups were subjected to toxicity evaluation using the "agar overlay" method described in Example I. Residual glutaraldehyde levels also were determined as described in Example I.

The results demonstrated that residual glutaraldehyde levels are reduced below 1 ppm; and there is only mild cytotoxicity at most, in the bioprostheses rinsed in a tris-containing solution according to the present invention. In contrast, bioprostheses that were not contacted with the amine (i.e., group #4) showed moderate to severe cytotoxicity.

EXAMPLE III

Extracted bovine ligaments are tanned by immersion in 0.625% (w/v) glutaraldehyde in an isotonic solution containing 5.39 grams/liter of the sodium salt of HEPES, 0.440 weight percent sodium chloride, and 2.6 grams/liter of $MgCl_2.6H_2O$ at room temperature.

Agarose-decylamine (AGDECYLAMINE TM, which is [Sepharose 4B]—NH—$(CH_2)_2$—$NH_2$) is purchased from Pharmacia P-L Biochemicals, Milwaukee, Wis. A slurry of the agarose-decylamine is prepared by adding HEPES buffer to the commercially prepared suspension. The ligament tissue prepared above is immersed in the slurry. The concentration of bound ligand (i.e., the amine compound) per milliliter of gel is specified by the agarose-decylamine manufacturer. An amount of gel sufficient to provide at least a 100-fold excess of free amine groups over the free residual aldehyde groups (in the tissue) is present in the slurry. The total volume of the slurry is approximately 100 mls. per 10 grams (wet weight) of bioprosthetic tissue immersed therein. A magnetic stirring bar is added to the container to stir the slurry so it remains homogeneous and circulates over the tissue. The tissue is immersed in fresh slurry as needed.

The tissue then is removed from the slurry, briefly rinsed (e.g., with saline or an aldehyde-free buffered solution) to remove residual agarose-decylamine material, and tested for cytotoxicity and residual glutaraldehyde as described in Example I. Tissue samples having 1 ppm or less residual glutaraldehyde and which are non-cytotoxic may be sterilized by conventional techniques (excluding contact with aldehydes) or otherwise further processed in preparation for surgical implantation, by known techniques. If the tissue is not needed immediately for implantation, it is packaged and stored, as described in Example I. A small amount of agarose-decylamine is added to the package, if desired.

TABLE I

| PRODUCTION RINSE PROCEDURES | PACKAGING SOLUTION USED | 3 × 5 MIN RINSES IN NORMAL SALINE | | QUICK NORMAL SALINE DIP | |
|---|---|---|---|---|---|
| | | A/O % CELL LYSIS | RESIDUAL EtOH (%) | A/O % CELL LYSIS | RESIDUAL EtOH (%) |
| 3 × 1 HR., 1 × 16 HR. Rinses in 0.1 M TRIS/50% EtOH | 0.1 M TRIS/50% EtOH | ~10% (mild cytotoxicity) | 1.4 | 20%-40% (mild to mod. cytotoxicity) | 3.5 |
| 5 × 1 HR., 1 × 16 HR. rinses in 0.1 M TRIS/50% EtOH | 0.1 M TRIS/50% EtOH | ~10% (mild cytotoxicity) | 1.25 | ~60% (moderate cytotoxicity) | 3.65 |
| 3 × 1 HR., 1 × 16 HR. Rinses in 0.1 M TRIS/70% EtOH | 0.1 M TRIS/70% EtOH | ~20% (mild cytotoxicity) | 1.55 | ~100% (severe cytotoxicity) | 4.75 |
| 5 × 1 HR., 1 × 16 HR. Rinses in 0.1 M TRIS/70% EtOH | 0.1 M TRIS/70% EtOH | ~20% (mild cytotoxicity) | 2.2 | ~100% (severe cytotoxicity) | 4.55 |
| 3 × 1 HR., 1 × 16 HR. Rinses in 0.1 M TRIS | 0.1 M TRIS/70% EtOH | 20-40% (mild to mod. cytotoxicity) | 1.4 | ~100% (severe cytotoxicity) | 3.25 |
| 5 × 1 HR., 1 × 16 HR. Rinses in 0.1 M TRIS | 0.1 M TRIS/50% EtOH | ~20% (mild cytotoxicity) | 1.2 | 80%-100% (mod. to severe cytotoxicity) | 2.3 |

TABLE II

| PRODUCTION RINSE PROCEDURES | PACKAGING SOLUTION USED | QUICK NORMAL SALINE DIP | | NO CLINICAL RINSE | |
|---|---|---|---|---|---|
| | | A/O % CELL LYSIS | RESIDUAL EtOH (%) | A/O % CELL LYSIS | RESIDUAL EtOH (%) |
| 3 × 1 HR., 1 × 16 HR. Rinses in 0.1 M TRIS/50% EtOH | 0.1 M TRIS | 0% (non-cytotoxic) | 0.075 | ~20% (mild cytotoxicity) | 0.13 |
| 5 × 1 HR., 1 × 16 HR. Rinses in 0.1 M TRIS/50% EtOH | 0.1 M TRIS | ~20% (mild cytotoxicity) | 0.1 | 0% (non-cytotoxic) | 0.125 |
| 3 × 1 HR., 1 × 16 HR. Rinses in 0.1 M TRIS/70% EtOH | 0.1 M TRIS | ~20% (mild cytotoxicity) | 0.065 | 20%–40% (mild to moderate cytotoxicity) | 0.112 |
| 5 × 1 HR., 1 × 16 HR. Rinses in 0.1 M TRIS/70% EtOH | 0.1 M TRIS | ~20% (mild cytotoxicity) | 0.015 | ~20% (mild cytotoxicity) | 0.145 |
| 3 × 1 HR., 1 × 16 HR. Rinses in 0.1 M TRIS | 0.1 M TRIS | 0% (non-cytotoxic) | N/A | ~20% (mild cytotoxicity) | N/A |
| 5 × 1 HR., 1 × 16 HR. Rinses in 0.1 M TRIS | 0.1 M TRIS | 0% (non-cytotoxic) | N/A | 0% (non-cytotoxic) | N/A |

We claim:

1. A method for decreasing residual tissue-fixing or tissue-sterilizing aldehyde levels in an implantable biological tissure previously contacted with said tissue-fixing or tissue-sterilizing aldehyde, comprising contacting said tissue with a rinsing solution to effect difusion of said aldehyde out of said tissue into said rinsing solution, said rinsing solution being water, saline or a buffered solution, and continuously or periodically contacting the rinsing solution with an aldehyde-reactive amine which is immobilized on a solid support, thus decreasing the concentration of said aldehyde in said rinsing solution and causing further diffusion of aldehyde out of said tissue.

2. The method of claim 1 wherein the concentration of amine in the rinsing solution is such that there is a stoichiometric excess of amino groups over the residual aldehyde groups.

3. The method of claim 2 wherein the rinsing solution comprises more than a 100-fold excess of amino groups over residual aldehyde groups.

4. The method of claims 1 or 2 wherein the amine is a primary or a secondary amine.

5. The method of claim 4 wherein said amine is an aliphatic or aromatic primary amine.

6. The method of claim 5 wherein the amine is an amino acid.

7. The method of claim 5 wherein the amine is tris(hydromethyl)aminomethane.

8. The method of claim 1 wherein the aldehyde is selected from the group consisting of glutaraldehyde, formaldehyde, glyoxal, or dialdehyde starch.

9. The method of claim 8 wherein the aldehyde is glutaraldehyde.

10. The method of claim 1 or 2 wherein the tissue is immersed in a volume of rinsing solution which is sufficient to promote efficient diffusion of said aldehyde out of said tissue.

11. The method of claim 10 wherein the tissue is immersed in about 100 mls of the rinsing solution per 10 grams (wet weight) of tissue.

12. The method of claims 1 or 2 wherein the temperature of the rinsing solution is maintained at between about 4° C. and about 45° C.

13. The method of claim 12 wherein the temperature of the rinsing solution is maintained at about 35±2° C.

14. The method of claims 1 or 2 wherein the pH of the rinsing solution is maintained between about 7.0 and about 7.6.

15. The method of claim 14 wherein the pH is maintained between about 7.1 and 7.4.

16. The method of claim 1 wherein the bioprosthetic tissue is derived from a source selected from the group consisting of bovine, porcine, equine, ovine, kangaroo, rabbit, or human tissues.

17. The method of claims 1 or 16 wherein the tissue is selected from the group consisting of pericardial tissue, dura mater, fascia lata, amnion, tendon, ligament, cartilage, collagen, arteries, veins, skin patches, and bone.

18. The method of claim 1 wherein the tissue is subjected to a calcification mitigation treatment.

19. The method of claim 1 wherein the tissue is subjected to a sterilization treatment.

20. The method of claim 1 or 2 wherein the tissue is contacted with the rinsing solution until residual aldehyde levels have been decreased to a level at which said bioprosthetic tissue is substantially non-cytotoxic.

21. The method of claim 20 wherein residual aldehyde levels have been decreased below about 1 part per million.

22. The method of claim 1 wherein said solid support is selected from agarose or polyacrylamide.

23. The method of claim 22 wherein said solid support is agarose activated by treatment with cyanogen bromide, and said amine is a diamine which is bound to said support by reaction with the bound cyanogen bromide.

24. The method of claim 22 wherein said solid support is agarose having a free carboxyl group-containing ligand attached thereto, and said amine is a diamine which is bound to said solid support using a carbodiimide coupling reagent.

25. The method of claim 23 or 24 wherein said diamine is ethylenediamine, lysine, hydroxylysine, or polylysine.

26. The method of claim 24 wherein said solid support having a free carboxyl group-containing ligand attached thereto is agarose having 6-amino-hexanoic acid coupled thereto, carboxymethyl agarose, or carboxyl terminal agarose.

27. The method of claim 22 wherein said solid support having an amine immobilized thereon is selected from the group consisting of agarose-butylamine, agarose-decylamine, agarose-ethylamine, agarose-adipic acid hydrazide, agarose having 1,6-diaminohexane coupled thereto, arginine-agarose, lysine-agarose, amino terminal agarose, aminoethyl polyacrylamide gels, or agarose having polylysine attached thereto.

28. The method of claim 1 wherein said free amino groups are present in an amount such that there is a stoichiometric excess of free amino groups over the residual aldehyde groups.

29. The method of claim 28 wherein said free amino groups are present in more than a 100-fold excess over the residual aldehyde groups.

30. The method of claim 1 wherein said amine immobilized on said support is added to said rinsing solution to form a slurry, and said tissue is immersed in the slurry.

31. The method of claim 30 wherein said tissue is immersed in about 100 mls. of said slurry per 10 grams (wet weight) of said tissue, and said slurry is circulated around said tissue.

32. The method of claim 1 wherein the rinsing solution is substantially amine-free.

* * * * *

UNITED STATES PATENT AND TRADEMARK OFFICE
CERTIFICATE OF CORRECTION

PATENT NO. : 4,786,287

DATED : November 22, 1988

INVENTOR(S) : Nashef et al.

It is certified that error appears in the above-identified patent and that said Letters Patent is hereby corrected as shown below:

Col. 8, line 27, "solid-matrix" should be --solid matrix--.

Col. 9, line 32, "temoeratures" should be --temperatures--;

Col. 9, line 59, "comorising" should be --comprising--;

Col. 13, line 26, "tissure" should be --tissue--;

Col. 13, line 28, "difusion" should be --diffusion--;

Col. 13, line 51, "dromethyl)aminomethane" should be --droxymethyl)aminomethane--.

Signed and Sealed this

Seventeenth Day of April, 1990

*Attest:*

HARRY F. MANBECK, JR.

*Attesting Officer*  *Commissioner of Patents and Trademarks*